United States Patent
Thakur et al.

(10) Patent No.: US 10,441,213 B2
(45) Date of Patent: Oct. 15, 2019

(54) DISCRIMINATION OF APNEA TYPE BY MEDICAL DEVICE

(71) Applicant: Cardiac Pacemakers, Inc., St. Paul, MN (US)

(72) Inventors: Pramodsingh Hirasingh Thakur, Woodbury, MN (US); David J. Ternes, Roseville, MN (US); Stephen B. Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 77 days.

(21) Appl. No.: 15/708,586

(22) Filed: Sep. 19, 2017

(65) Prior Publication Data
US 2018/0064390 A1    Mar. 8, 2018

Related U.S. Application Data

(63) Continuation of application No. 15/213,120, filed on Jul. 18, 2016, now Pat. No. 9,788,782, which is a
(Continued)

(51) Int. Cl.
*A61B 5/00* (2006.01)
*A61B 5/08* (2006.01)
(Continued)

(52) U.S. Cl.
CPC ........ *A61B 5/4818* (2013.01); *A61B 5/02405* (2013.01); *A61B 5/053* (2013.01);
(Continued)

(58) Field of Classification Search
CPC ........ A61B 2560/0475; A61B 5/02405; A61B 5/053; A61B 5/0809; A61B 5/0826;
(Continued)

(56) References Cited

U.S. PATENT DOCUMENTS

| 7,225,021 B1 | 5/2007 | Park |
| 7,678,058 B2 | 3/2010 | Patangay et al. |

(Continued)

FOREIGN PATENT DOCUMENTS

| WO | WO-2006066337 A1 | 6/2006 |
| WO | WO-2012155257 A1 | 11/2012 |
| WO | WO-2015153044 A1 | 10/2015 |

OTHER PUBLICATIONS

"U.S. Appl. No. 14/638,142, Non Final Office Action dated Nov. 27, 2015", 5 pgs.
(Continued)

*Primary Examiner* — George Manuel
(74) *Attorney, Agent, or Firm* — Schwegman Lundberg & Woessner, P.A.

(57) ABSTRACT

Disclosed herein, among other things, are methods and apparatus related to identification of apnea type. One aspect of the present subject matter provides a method for real-time apnea discrimination. The method includes sensing an impedance-based tidal volume signal to monitor a respiratory cycle of a patient, and detecting a reduction in tidal swing using the sensed impendence to detect an apnea event. When the apnea event is detected, a shape of the sensed signal is compared to a stored signal shape to determine whether the apnea event is primarily an obstructive sleep apnea (OSA) event or primarily a central sleep apnea (CSA) event, in various embodiments.

20 Claims, 8 Drawing Sheets

Related U.S. Application Data continuation of application No. 14/638,142, filed on Mar. 4, 2015, now Pat. No. 9,402,563.

(60) Provisional application No. 61/975,084, filed on Apr. 4, 2014.

(51) Int. Cl.
| | | |
|---|---|---|
| *A61B 7/02* | (2006.01) | |
| *A61B 5/053* | (2006.01) | |
| *A61B 5/024* | (2006.01) | |
| *A61B 7/04* | (2006.01) | |

(52) U.S. Cl.
CPC .......... *A61B 5/0809* (2013.01); *A61B 5/0826* (2013.01); *A61B 5/7275* (2013.01); *A61B 5/7278* (2013.01); *A61B 5/7282* (2013.01); *A61B 5/742* (2013.01); *A61B 7/02* (2013.01); *A61B 7/04* (2013.01); *A61B 2560/0475* (2013.01)

(58) Field of Classification Search
CPC ... A61B 5/4818; A61B 5/7275; A61B 5/7278; A61B 5/7282; A61B 5/742; A61B 7/02; A61B 7/04
See application file for complete search history.

(56) References Cited

U.S. PATENT DOCUMENTS

| | | | |
|---|---|---|---|
| 8,551,010 | B2 | 10/2013 | Pu et al. |
| 8,560,072 | B2 | 10/2013 | Caparso et al. |
| 9,402,563 | B2 | 8/2016 | Thakur et al. |
| 2008/0269583 | A1 | 10/2008 | Reisfeld |
| 2010/0298733 | A1 | 11/2010 | Kwok et al. |
| 2011/0061647 | A1* | 3/2011 | Stahmann ............ A61B 5/0031 128/202.16 |
| 2013/0041269 | A1 | 2/2013 | Stahmann et al. |
| 2013/0060149 | A1 | 3/2013 | Song et al. |
| 2014/0188006 | A1* | 7/2014 | Alshaer ................ A61B 5/7282 600/586 |
| 2015/0119740 | A1* | 4/2015 | Hernandez ........... A61B 5/0476 600/529 |
| 2015/0282738 | A1 | 10/2015 | Thakur et al. |
| 2016/0324467 | A1 | 11/2016 | Thakur et al. |

OTHER PUBLICATIONS

"U.S. Appl. No. 14/638,142, Notice of Allowance dated Mar. 31, 2016", 7 pgs.

"U.S. Appl. No. 14/638,142, Response filed Feb. 29, 2016 to Non Final Office Action dated Nov. 27, 2015", 6 pgs.

"U.S. Appl. No. 15/213,120, Non Final Office Action dated Feb. 23, 2017", 6 pgs.

"U.S. Appl. No. 15/213,120, Notice of Allowance dated Jun. 14, 2017", 7 pgs.

"U.S. Appl. No. 15/213,120, Response filed May 23, 2017 to Non Final Office Action dated Feb. 23, 2017", 6 pgs.

"International Application Serial No. PCT/US2015/018669, International Preliminary Report on Patentability dated Oct. 13, 2016", 9 pgs.

"International Application Serial No. PCT/US2015/018669, International Search Report dated Jun. 1, 2015", 4 pgs.

"International Application Serial No. PCT/US2015/018669, Written Opinion dated Jun. 1, 2015", 8 pgs.

"Remede implantable device system shows "promising" results in the treatment of central sleep apnoea, pilot study shows", Cardiac Rhythm News, http://www.cxvascular.com/crn-latest-news/cardiac-rhythm-news---latest-news/remede-imp . . . 2 pages, latest print date Mar. 3, 2015.

Abraham, W.T., et al., "The Effects of Chronic Implanted Transvenous Phrenic Nerve Stimulation in Central Sleep Apnea: The Remede System Pilot Study", Lipids and Inflammation / Heart Failure: Basic Mechanisms; European Heart Journal, (Aug. 1, 2013), 769.

Argod, Jerome, et al., "Differentiating Obstructive and Central Sleep Respiratory Events through Pulse Transit Time", Am J Respir Crit Care Med; 158, (1998), 1778-1783.

Dimarco, Anthony F., et al., "Phrenic Nerve Pacing Via Intramuscular Diaphragm Electrodes in Tetraplegic Subjects", Chest. 2005;127(2):671-678, Feb. 2005.

Franke, Manfred, et al., "Selective Nerve Stimulation Using Presynaptic Terminal Depletion Block", U.S. Appl. No. 61/928,732, filed Jan. 17, 2014.

Kaiser, Chris, "Device Cuts Central Sleep Apnea Events", MedPage Today; http://www.medpagetoday.com/MeetingCoverage/HFSA/41796?xid=nl_mpt_DHE_2013-09-24, (Sep. 23, 2013), 3.

Mietus, JE, et al., "Detection of Obstructive Sleep Apnea from Cardiac Interbeat Interval Time Series", Physionet, http://www.physionet.org/physiotools/apdet/apdet.shtml, 5 pages, latest print date Mar. 2, 2015.

Teerlink, John, et al., "ATOMIC-AHF: Acute Treatment with Omecamtiv Mecarbil to Increase Contractility in Acute Heart Failure: Results from ATOMIC-AHF", European Society of Cardiology; Session No. 709, (2013), 1-3.

Ternes, David J., et al., "Methods and Apparatus for Apnea Therapy Stimulation", U.S. Appl. No. 61/975,090, filed Apr. 4, 2014.

Thomas, Robert Joseph, et al., "Differentiating obstructive from central and complex sleep apnea using an automated electrocardiogram-based method", SLEEP, vol. 30, No. 12, 2007, XP055190891, (Jul. 2007), 1756-1769.

University Hospitals, Case Medical Center, "Electronic stimulation therapy for obstructive sleep apnea is safe, effective, new study suggests", Science Daily; www.sciencedaily.com/releases/2013/06/130605144316.htm, (Jun. 5, 2013), 1.

\* cited by examiner

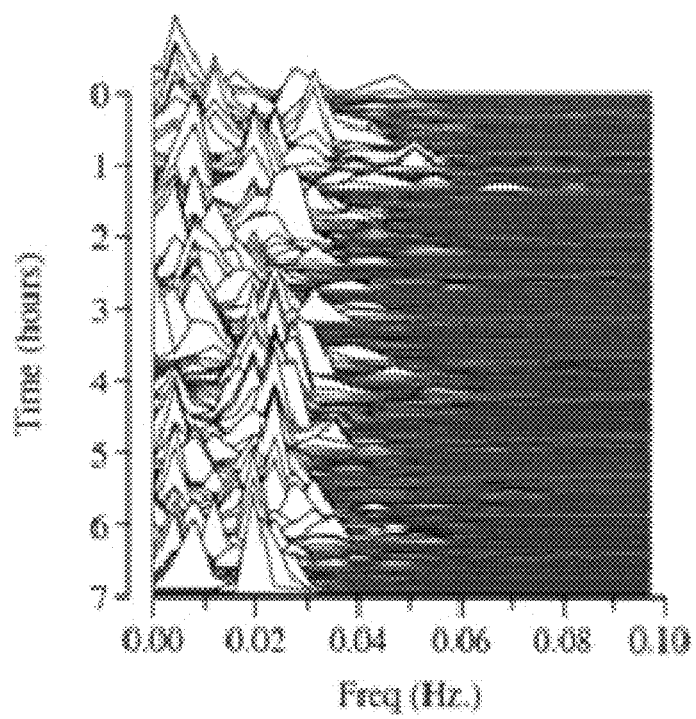
Fig. 5A OSA
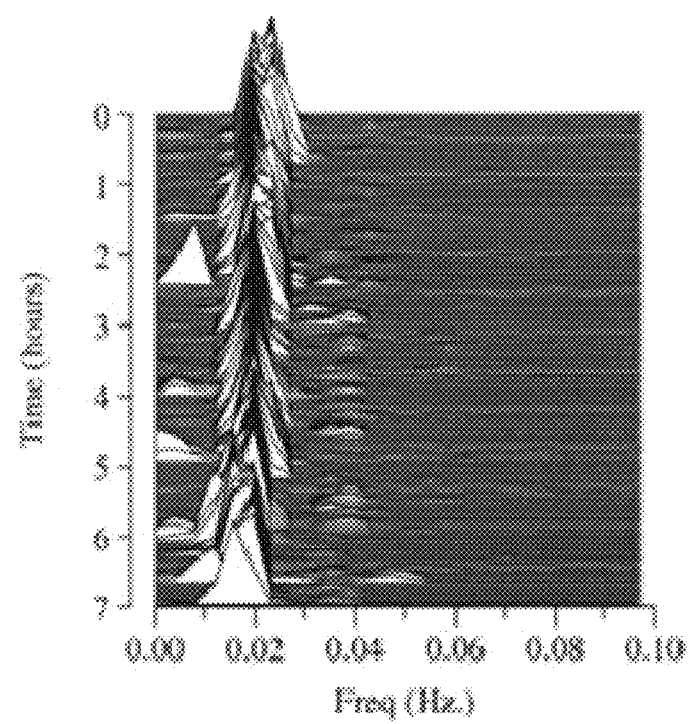
Fig. 5B CSA

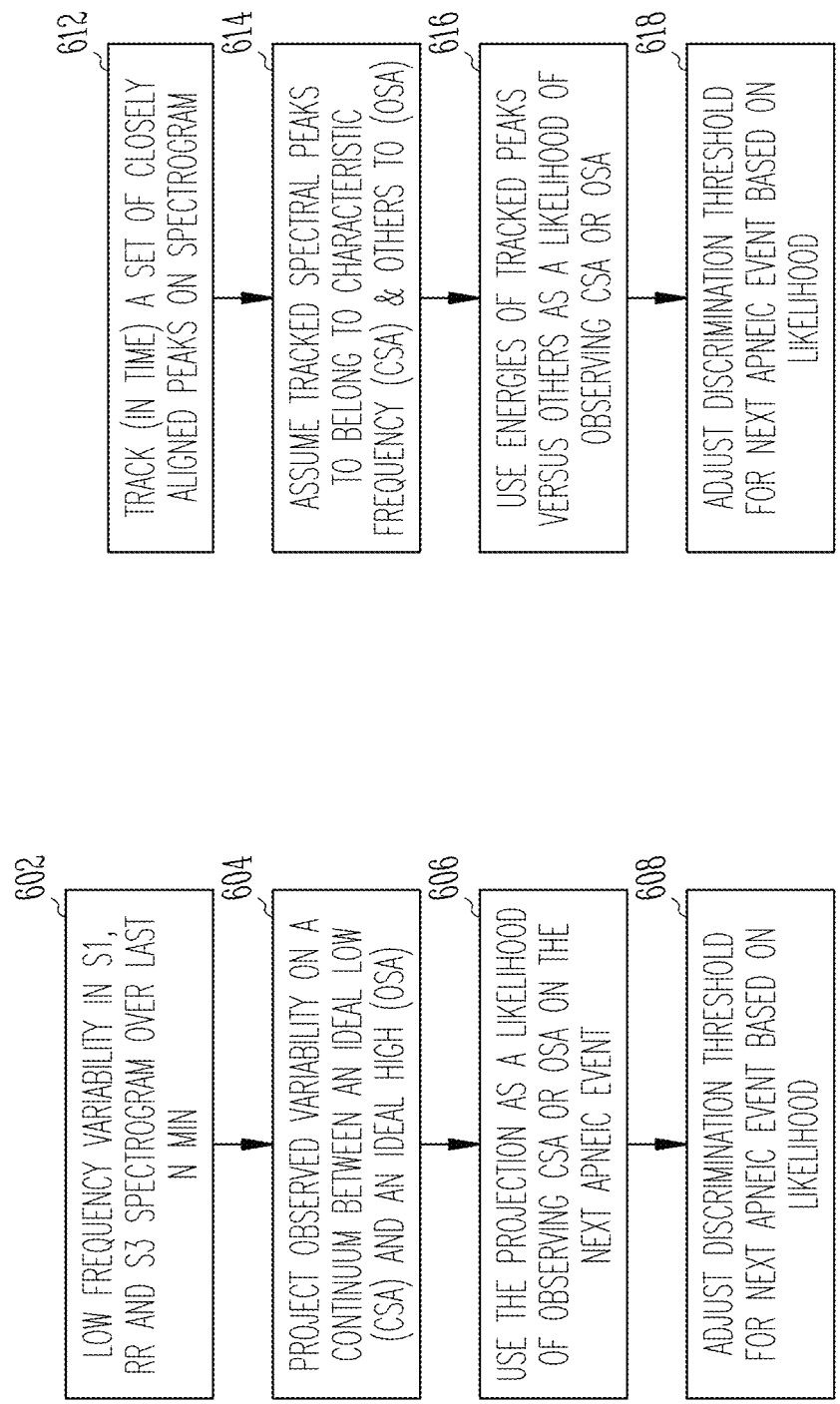

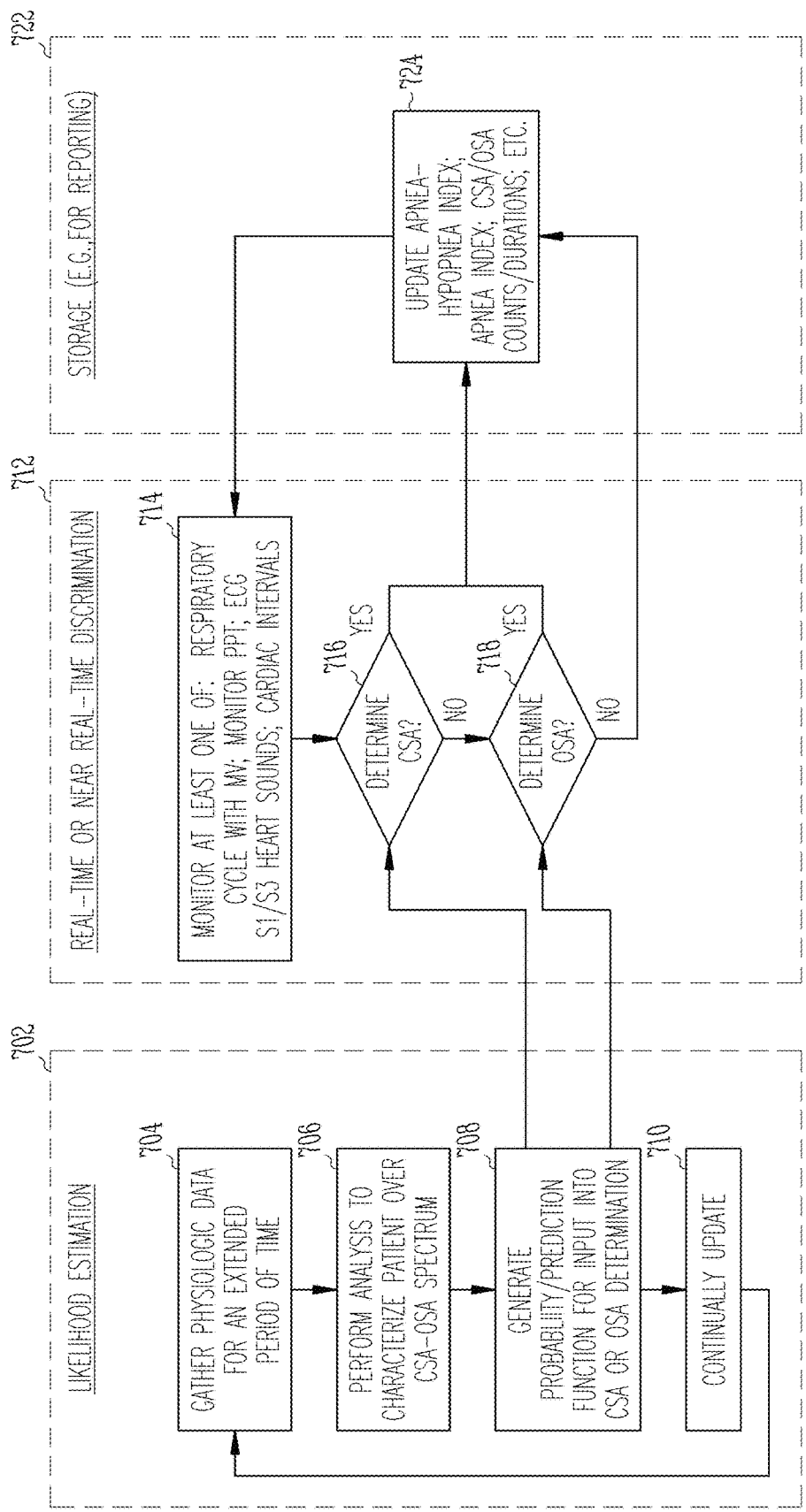

DISCRIMINATION OF APNEA TYPE BY MEDICAL DEVICE

CLAIM OF PRIORITY

This application is a continuation of U.S. application Ser. No. 15/213,120, filed Jul. 18, 2016, which is a continuation of U.S. application Ser. No. 14/638,142, filed Mar. 4, 2015, now issued as U.S. Pat. No. 9,402,563, which claims the benefit of priority under 35 U.S.C. § 119(e) of U.S. Provisional Patent Application Ser. No. 61/975,084, filed on Apr. 4, 2014, which is herein incorporated by reference in its entirety.

CROSS REFERENCE TO RELATED APPLICATION

This application is related to commonly assigned, U.S. Patent Application Ser. No. 61/975,090, entitled "METHODS AND APPARATUS FOR APNEA THERAPY STIMULATION", filed on Apr. 4, 2014, which is hereby incorporated by reference in its entirety.

TECHNICAL FIELD

This application relates generally to medical devices and, more particularly, to systems, devices and methods related to discrimination of apnea type.

BACKGROUND

Respiratory diseases include disorders that affect breathing during sleep. Examples of respiratory disorders include central sleep apnea (CSA) and obstructive sleep apnea (OSA). Sleep apnea refers to the cessation of breathing during sleep. CSA is associated with incorrect sensing of carbon dioxide or oxygen levels in the blood. If nerve receptors do not send the correct neural signals, in essence deceiving the brain by reporting incorrect levels of carbon dioxide or oxygen, an incidence of CSA can occur. OSA is associated with an obstruction of the upper airway. Both CSA and OSA have serious health consequences, including association with cardiac arrhythmias and worsening heart failure. CSA and OSA can occur separately or together in a given patient during the night.

Typically, therapy for CSA is not effective for OSA, and therapy for OSA is not effective for CSA. Therefore, there is a need in the art for real-time apnea discrimination.

SUMMARY

Disclosed herein, among other things, are methods and apparatus related to identification of apnea type. One aspect of the present subject matter provides a method for real-time apnea discrimination. The method may include sensing an impedance-based tidal volume signal to monitor a respiratory cycle of a patient, and detecting a reduction in tidal swing using the sensed impendence to detect an apnea event. When the apnea event is detected, a shape of the sensed signal is compared to a stored signal shape to determine whether the apnea event is primarily an obstructive sleep apnea (OSA) event or primarily a central sleep apnea (CSA) event, in various embodiments.

One aspect of the present subject matter provides a medical device for apnea discrimination. The device may include a sensor configured to sense an impedance-based tidal volume signal to monitor a respiratory cycle of a patient and a processor adapted to be connected to the sensor. The processor may be configured to detect a reduction in tidal swing using the sensed impendence to detect an apnea event and to compare a shape of the sensed signal to a stored signal shape to determine whether the detected apnea event is primarily an obstructive sleep apnea (OSA) event or primarily a central sleep apnea (CSA) event, in various embodiments.

One aspect of the present subject matter provides a medical device for apnea discrimination. The device may include a sensor configured to sense a parameter related to heart sounds of a patient and a processor adapted to be connected to the sensor. The processor may be configured to use the sensed parameter to determine whether a detected apnea event is primarily an obstructive sleep apnea (OSA) event or primarily a central sleep apnea (CSA) event.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 5A-5C illustrate graphical diagrams showing examples of signals that may be used to discriminate OSA and CSA, according to various embodiments of the present subject matter.

FIGS. 6A-6B illustrate flow diagrams for an example of methods of adjusting an apnea discrimination threshold, according to various embodiments of the present subject matter.

FIG. 7 illustrates a flow diagram for an example of a method of identifying apnea, according to various embodiments of the present subject matter.

DETAILED DESCRIPTION

Figure 1:
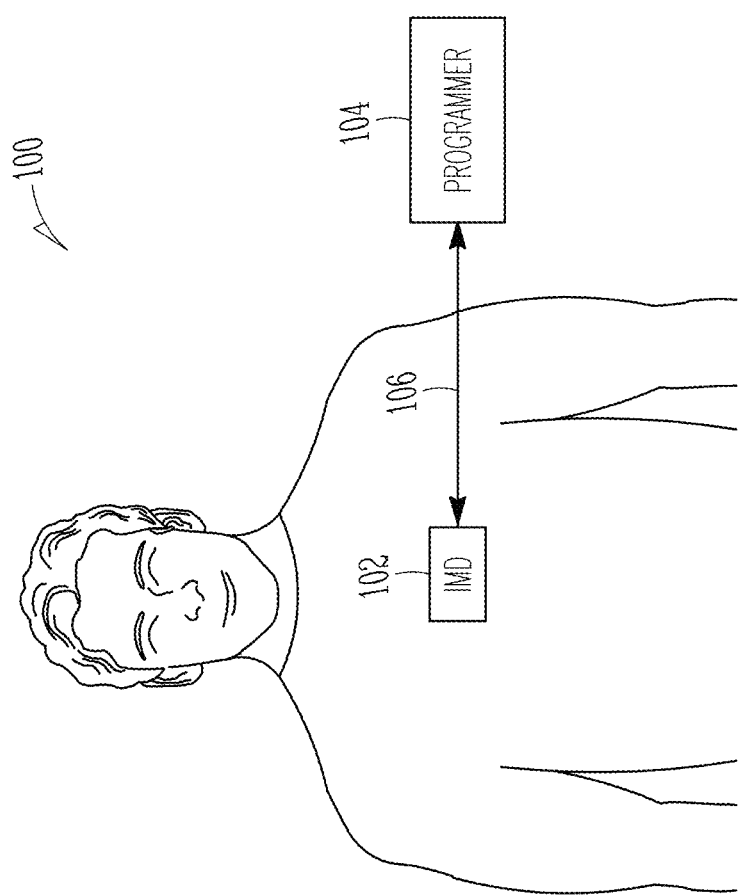
FIG. 1 illustrates an example of a therapy system with a programmer.

The following detailed description refers to subject matter in the accompanying drawings which show, by way of illustration, specific aspects and embodiments in which the present subject matter may be practiced. These embodiments are described in sufficient detail to enable those skilled in the art to practice the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Obstructive sleep apnea (OSA) and central sleep apnea (CSA) are driven by different causes and hence target therapies are different for each type of sleep apnea. Continuous positive airway pressure (CPAP) works well for OSA but is generally not effective for treating CSA. Diaphragmatic stimulation can be used to treat CSA but is generally not effective for OSA, since respiratory drive already exists during OSA. In addition, patients may not experience OSA or CSA episodes exclusively, as typically they may experience both OSA and CSA episodes throughout the night. Presently, the classification (or discrimination) of a patient into OSA or CSA patient is largely based on predominant prevalence of the apnea type during the night. However, even patients that experience largely one type of apnea and are classified as that apnea type, do experience occasional apneic episodes that are of the other type. In some cases, it may be valuable to not apply OSA therapy for sparse CSA episodes in OSA patients or vice versa. There is a challenge to quickly identify what type of apnea event is in progress, so proper treatment can be applied in a timely manner. Therefore, there is a need in the art for real-time apnea discrimination, so that the proper therapy can be delivered for the episode.

Various examples provided herein use an algorithm to characterize apnea and learn likelihoods of observing the types of apnea specific to an individual patient. The system may use that probability analysis to assist in determining type of apnea, in various embodiments. Disclosed herein, among other things, are methods and apparatus related to identification of apnea type. One aspect of the present subject matter provides a method for real-time or near real-time apnea discrimination. These terms indicate that, although there may be some processing delays, the apnea discrimination is able to process the apneic events as they occur without an observable delay (e.g. real time) or with observable delays that are insignificant for processing the apneic events as they occur (near real time). The method may include sensing an impedance-based tidal volume signal to monitor a respiratory cycle of a patient, and detecting a reduction in tidal swing using the sensed impendence to detect an apnea event. When the apnea event is detected, a shape of the sensed signal is compared to a stored signal shape to determine whether the apnea event is primarily an OSA event or primarily a CSA event, in various embodiments. This discrimination is done in real time based on features from early portions of the apnea event, so that the proper therapy can be provided in a timely manner to assist in treating the event.

Disclosed herein, among other things, are methods and apparatus related to identification of apnea type. One aspect of the present subject matter provides a method for real-time apnea discrimination. The method may include sensing an impedance-based tidal volume signal to monitor a respiratory cycle of a patient, and detecting a reduction in tidal swing using the sensed impendence to detect an apnea event. When the apnea event is detected, a shape of the sensed signal is compared to a stored signal shape to determine whether the apnea event is primarily an obstructive sleep apnea (OSA) event or primarily a central sleep apnea (CSA) event, in various embodiments.

According to various embodiments, the stored signal shape may include a normal tidal swing shape for the patient, a stored prior OSA waveform template, a sine wave (as a surrogate for CSA template), and/or a square wave (as a surrogate for OSA template). If the shape of the sensed signal is similar to the normal tidal swing shape, the apnea event is determined to be primarily a CSA event in various embodiments. In various embodiments, if the shape of the sensed signal is not similar to the normal tidal swing shape, the apnea event is determined to be primarily an OSA event. There are various methods or algorithms that may be implemented to analyze the similarity between the signals. For example, a statistical analysis may be performed on the signals to determine a calculated similarity value, and this similarity value may be compared to a similarity threshold to make a determination that the signals are similar. Various embodiments further include calculating likelihood for each apnea event based on historical prevalence of CSA events and OSA events for the patient. Some embodiments include using the calculated likelihood to determine whether the apnea event is primarily an obstructive sleep apnea (OSA) event or primarily a central sleep apnea (CSA) event. Therapy is provided to the patient based on the determination, in various embodiments.

One aspect of the present subject matter provides a medical device for apnea discrimination. The device may include a sensor configured to sense an impedance-based tidal volume signal to monitor a respiratory cycle of a patient and a processor adapted to be connected to the sensor. The processor may be configured to detect a reduction in tidal swing using the sensed impendence to detect an apnea event and to compare a shape of the sensed signal to a stored signal shape to determine whether the detected apnea event is primarily an obstructive sleep apnea (OSA) event or primarily a central sleep apnea (CSA) event, in various embodiments.

One aspect of the present subject matter provides a medical device for apnea discrimination. The device may include a sensor configured to sense a parameter related to heart sounds of a patient and a processor adapted to be connected to the sensor. The processor may be configured to use the sensed parameter to determine whether a detected apnea event is primarily an obstructive sleep apnea (OSA) event or primarily a central sleep apnea (CSA) event. Additionally or alternatively, the processor may be configured to use the sensed parameter to determine whether the patient may be classified as primarily experiencing OSA or as primarily experiencing CSA. In addition to determining the patient's primary apnea type (OSA or CSA), or as a separate determination, the processor may be configured to use the sensed parameter to determine a mix or ratio of OSA and CSA for that individual patent. The mix or ratio may be displayed or otherwise communicated to a clinician for diagnostic assistance. In some cases, the display may present the mix or ratio of OSA and CSA in textual format, as a trend, or in any other suitable manner.

According to various embodiments, the processor may be configured to use variability in low frequency components of a spectrum of at least one of R-R intervals, S1 amplitude, S2 amplitude, S3 amplitude or systolic time intervals over time to determine prevalence of primarily OSA events and primarily CSA events for the patient. In various embodiments, examples of systolic time intervals include: pre-ejection period (PEP): Q-S1, R-S1, ejection time, diastolic interval and S1-S2 interval. Various embodiments include any of these timing intervals or an entire R-R interval.

The processor may be configured to conduct a time-frequency decomposition of the signal of interest using any standard time frequency methods, such as short term Fourier transform, wavelet transform, Wigner-Ville transform, etc. to obtain a spectrogram of the signal over some period of time which could range from the last few minutes, to the last few hours, to the last few days. The processor may be configured to use the variability along the frequency axis on the spectrogram to determine a likelihood of observing CSA or OSA on the next apnea event, in various embodiments. In various embodiments, the processor may be configured to adjust a discrimination threshold for the next apnea event based on the determined likelihood. The processor may be configured to track a set of consistent spectral peaks on the spectrogram and use energies of tracked peaks to determine relative prevalence of primarily OSA events and primarily CSA events for the patient, in an embodiment. Dynamic programming algorithms such as the Viterbi algorithm may be employed to track the set of most consistent peaks over time. Such algorithms usually define a cost-function based on the energies of candidate peaks and the offsets (in frequencies) between peaks across time steps, and use minimization of the cost function to derive a set of consistent peaks across time. For example, a consistent peak track could be defined as a collection of peaks over time (one peak at every time step on the spectrogram) that maximizes the sum of energies at those peaks and minimizes the absolute sum of the differences in frequencies between peaks at successive time steps. In various embodiments, the processor may be configured to use energy of the tracked peaks relative to total spectral energy to determine a likelihood of observing CSA or OSA on the next apnea event. The processor may be configured to adjust a discrimination threshold for the next apnea event based on the determined likelihood, according to various embodiments. For example, if the total energy at the tracked set of peaks is 80% of the total spectral energy over the last N hours, then the a priori likelihood of observing a CSA event at the next apneic episode is 80%. Thus, the next apneic event is declared to be an OSA event only if similarity of the early portions of the tidal volume signal to an OSA template is at least 4 (80/20) times the similarity to a CSA template. In this way, the detection for the current event is biased towards being labeled a CSA given that higher likelihood of observing a CSA based on the spectrogram analysis.

Some embodiments may include a memory to store historical data of CSA events and OSA events for the patient, and the processor may be configured to calculate likelihood for each apnea event based on the historical data. In various embodiments, the processor may be configured to use the calculated likelihood to determine whether the next apnea event is likely to be primarily an obstructive sleep apnea (OSA) event or primarily a central sleep apnea (CSA) event. For example, if a patient has historically experiences 80% CSA episodes and 20% OSA episodes over the last N hours or last N days, then the a priori likelihood of observing a CSA event at the next apneic episode is 80%.

In some embodiments, a confidence score may be assigned to the apneic classification over a period (N hours, for example) based upon the comparison of the stored historical data of CSA and OSA events for that patient over the period with a spectrogram-based assessment of prevalence of CSA and OSA over the same period. If there is a close match between the classification results (stored as historical data) and the spectrogram based estimates, the results are labeled as high confidence. If there is a mismatch between the assigned classification and spectrogram based assessment results are flagged as low confidence.

Figure 4:
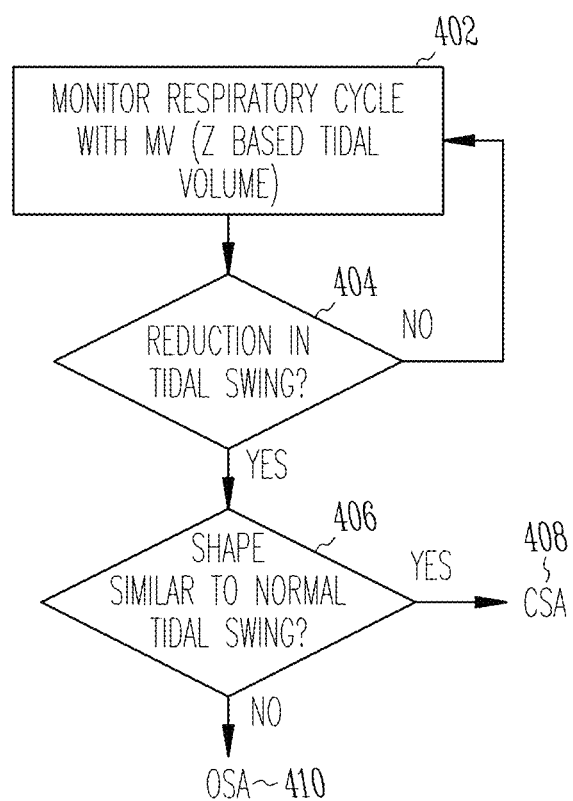
FIG. 4 illustrates a flow diagram for an example of a method of identifying apnea, according to various embodiments of the present subject matter.

FIG. 4 illustrates a flow diagram for an example of a method of identifying apnea, according to various embodiments of the present subject matter. At 402, a patient's respiratory cycle is monitored, such as with minute ventilation (MV) using Z-based tidal volume in an embodiment. Other parameters indicative of a patient's respiratory cycle may be monitored without departing from the scope of the present subject matter. If a reduction in tidal swing is detected at 404, an apnea event is detected and a shape of the reduced tidal swing signal is compared to a normal tidal swing at 406. If the shape is similar to normal tidal swing, the apnea event is primarily a CSA event at 408. If the shape is not similar to normal tidal swing, the apnea event is primarily an OSA event at 410. Various embodiments compare shape similarity to a stored prior OSA template. Further embodiments compare shape similarity to ideal sine waves as a surrogate for a CSA waveform template. Still further embodiments compare shape similarity to ideal square waves as a surrogate for an OSA waveform template.

In various embodiments, the present subject matter determines apnea and discriminates apnea type in a first portion of an apnea event, so that appropriate therapy can be applied in a timely manner. In one embodiment apnea is discriminated in the first 10 to 15 percent of an apnea episode. Other time periods can be used without departing from the scope of the present subject matter. In various embodiments, an a priori likelihood is developed from a prevalence of episodes determined from historical data, and the likelihood is used to discriminate current apnea events. According to various embodiments, shape of the monitored impedance characteristic is used to discriminate apnea events. For example, OSA changes the shape by flattening the characteristic. In one example, CSA has the same shape with a reduced magnitude.

Figure 5C:
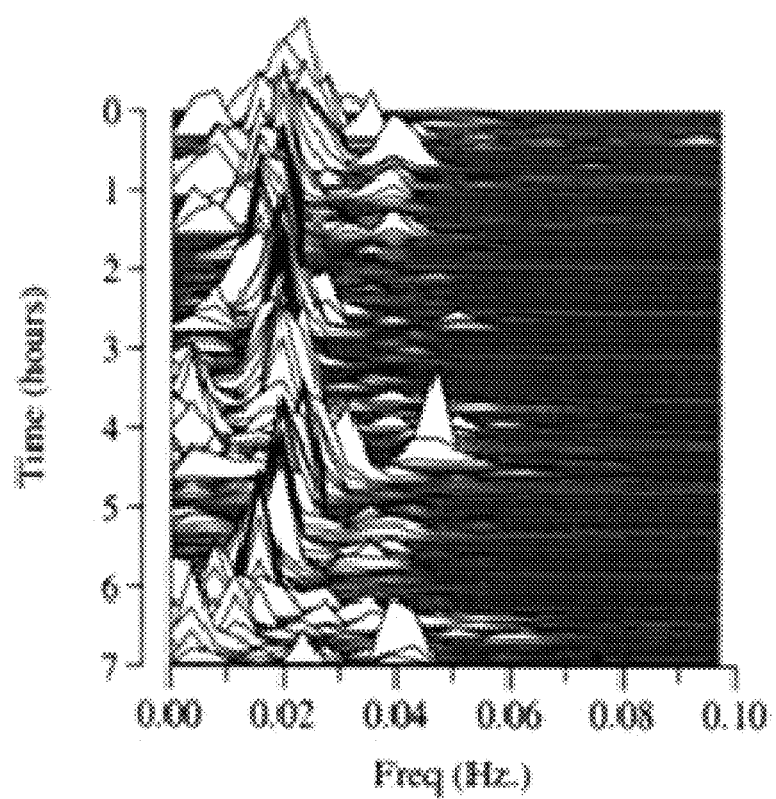

According to various embodiments, the present subject matter may use patency from an impedance-based tidal volume signal to discriminate OSA and CSA. Various embodiments may use a priori likelihoods for an apnea episode based upon the historic prevalence of the two types of apneas or long term (robust) analysis of historic data in a given patient, for apnea discrimination. The present subject matter may use an estimate of prevalence of CSA and OSA to assess the likelihood of the next apnea event, in an embodiment. Quantification of prevalence of CSA and OSA may be determined as discussed, including examining variability in Fourier transforms, in an embodiment FIGS. 5A-5C illustrate graphical diagrams showing examples of signals that may be used to discriminate OSA and CSA, according to various embodiments of the present subject matter. The depicted graphs show short term Fourier transforms of R-R intervals computed over short epochs at different points in time throughout the night, in various embodiments. In some embodiments, S1 amplitude, S2 amplitude, S3 amplitude or any systolic time intervals may be used as the signal of interest instead of R-R intervals. CSA episodes are usually associated with oscillations at a characteristic system frequency (which is below the respiration frequency of 0.1-0.3 Hz) resulting in Cheney stokes pattern. Cheney stokes oscillations lead to a waxing and waning of respiratory drive at the same characteristic frequency which in turn sets up oscillations at the Cheney stokes frequency in the intrathoracic pressures. Such an oscillatory pattern leads to oscillations in Heart rate, S1 amplitude, S2 amplitude, S3 amplitudes and time intervals (systolic and diastolic) that show up as a narrow band of spectral peaks at the characteristic Cheney stokes frequency on the spectrogram. On the other hand, in case of OSA episodes there are no oscillations at any characteristic frequency and hence, the spectral components in the low frequency region of the spectrogram are completely random. These expected profiles of CSA and OSA in the low frequency region of the spectrogram can be used to quantify the prevalence of CSA and OSA episodes over a given period. In FIG. 5A, variability in low frequency (below respiration)

components of R-R intervals is very high and is indicative of a primarily OSA apnea event in an embodiment. For example, various embodiments find that it is more likely that OSA dominates an event when there are greater amount of variability in the peaks. FIG. 5B shows an embodiment of a primarily CSA apnea event, as there is less variability observed in the peaks of the low frequency components. FIG. 5C illustrates an embodiment of a more complex profile, that includes both CSA and OSA. A set of peaks could be isolated over time that are closely located in frequency. Such a set would be characterized by low variation in frequency (due to constraint on the peaks being closely located in frequency) and thus would be characteristic of CSA portions of apneic episodes. The relative energies of peaks within this set relative to total spectral energy in the spectrogram could be indicative of the portion of apneic episodes within this time period that are CSA. In various embodiments, the spectral profiles depicted in FIGS. 5A-5C and their analysis may be used to set an a priori likelihood for the next apnea event for a patient.

In some embodiment any variable out of R-R interval, S1 amplitude, S2 amplitude, S3 amplitude, systolic or diastolic interval may be used as the signal of interest to perform the spectral analysis. In another embodiment, spectral analysis can be individually conducted on more than one of the variables and the results combined/averaged for a more robust estimation.

FIGS. 6A-6B illustrate flow diagrams for an example of methods of determining a priori likelihood of next apneic event based on the profile of the low frequency portion of the spectrogram over the last N minutes, or last N hours or last N days by adjusting an apnea discrimination threshold, according to various embodiments of the present subject matter. FIG. 6A illustrates an example of a method using low frequency spectrogram variability to adjust an apnea discrimination threshold, in an embodiment. At 602, low frequency variability of an impedance-based tidal volume signal spectrogram is monitored over a programmable time period (N min or N days or N hours). Observed variability is projected on a continuum between an ideal low level (indicative of CSA) and an ideal high level (indicative of OSA), at 604. At 606, the projection is used as a likelihood of observing CSA or OSA for the next apnea event. At 608, the discrimination threshold is adjusted for the next apnea event based on the likelihood, in various embodiments. For example, if spectrogram analysis indicates that the prevalence of CSA was 80% over the last N hours, then the a priori likelihood of observing the next apneic event as CSA is 80% and threshold is set such that similarity of the next event to an OSA template should be at least four times the similarity to a CSA template in order for it to be labeled OSA. In this way, the classification of the next event is biased towards being labeled CSA in light of the high a priori likelihood of it being a CSA based on spectrogram analysis.

FIG. 6B illustrates an example of a method using alignment of peaks on a spectrogram to adjust an apnea discrimination threshold, in an embodiment. At 612, a set of closely aligned peaks on a spectrogram are tracked in time. Dynamic programming algorithms such as the Viterbi algorithm may be employed to track the set of most consistent over time. Such algorithms usually define a cost-function based on the energies of candidate peaks and the offsets (in frequencies) between peaks across time steps and use minimization of the cost function to derive a set of consistent peaks across time. For example, a consistent peak track could be defined as a collection of peaks over time (one peak at every time step on the spectrogram) that maximizes the sum of energies at those peaks and minimizes the absolute sum of the differences in frequencies between peaks at successive time steps. At 614, tracked spectral peaks are categorized as having a characteristic frequency (CSA) and other peaks are categorized as OSA. Energy of tracked peaks versus other peaks is used as a likelihood of observing CSA or OSA, at 616. At 618, the discrimination threshold is adjusted for the next apnea event based on the likelihood, in various embodiments.

FIG. 7 illustrates a flow diagram for an example of a method of identifying apnea, according to various embodiments of the present subject matter. The depicted method embodiment includes three parts: likelihood estimation 702, real-time discrimination 712 and storage 722. At 704, likelihood estimation includes gathering physiologic data over a programmable time period. Analysis is performed on the gathered data to characterize apnea events for a patient over a CSA-OSA spectrum, at 706. At 708, a probability and/or prediction function is generated for input into a CSA or OSA determination. The process is updated at 710. The process can be updated programmably, periodically, intermittently and/or continually, in various embodiments.

At 714, real-time discrimination includes monitoring at least one of: respiratory cycle with MV, PPT, ECG, S1/S3 heart sounds and cardiac intervals. If CSA is determined at 716, an apnea-hypopnea index is updated at 724. In various embodiments, an apnea index includes CSA and OSA counts, durations, etc. If no CSA is determined at 716, then a determination is made of OSA at 718. If OSA is determined at 718, an apnea-hypopnea index is updated at 724. If no OSA is determined at 716, then an apnea-hypopnea index is updated at 724. Additional implanted sensors may be used to further augment CSA/OSA classification, such as spectral analysis of S1/S3 heart sounds (amplitudes), pulse transit time (ECG/cervical impedance plethysmography), ECG-based spectral analysis, and cardiac interbeat interval time series, in various embodiments. Once apnea is determined and discriminated, the appropriate therapy can be applied in a closed loop system, such as the apnea therapy in co-pending, commonly assigned, U.S. Patent Application Ser. No. 61/975,090, entitled "METHODS AND APPARATUS FOR APNEA THERAPY STIMULATION", filed on Apr. 4, 2014, which is hereby incorporated by reference in its entirety.

The present subject matter provides a diagnostic tool for clinicians to determine extent of apnea (e.g. apnea-hypopnea index (AHI)), to determine type of apnea (OSA, CSA, or where the patient falls on the central-obstructive apnea spectrum), and/or to provide clinician guidance on determining that patient's therapy (CPAP type/settings; phrenic or hypoglossal stimulation; etc.). This diagnostic tool can be provided in any medical device including, for example, an implantable stimulator, (e.g. pacemaker, implantable cardioverter defibrillator (ICD), subcutaneous ICD (S-ICD), cardiac resynchronization therapy (CRT) device, or nerve stimulator such as a vagal nerve stimulator, a carotid sinus stimulator, a hypoglossal nerve stimulator, or a phrenic nerve stimulator), an implantable diagnostic device or monitor, a wearable device (e.g. patches or vests), or external medical devices.

FIG. 1 illustrates an example of stimulation system 100. The system may include an external medical device, such as external patch based sensors, in various embodiments. Other types of external medical devices may be used for apnea discrimination without departing from the scope of the present subject matter. Various embodiments of the system may include an implantable medical device (IMD) 102 implanted into a patient's tissue and an external device such as a programmer 104 external to the patient's body. The programmer 104 and the IMD 102 may communicate via a telemetry link 106. Embodiments of the system without sensing are included within the scope of the present subject matter.

Figure 2:
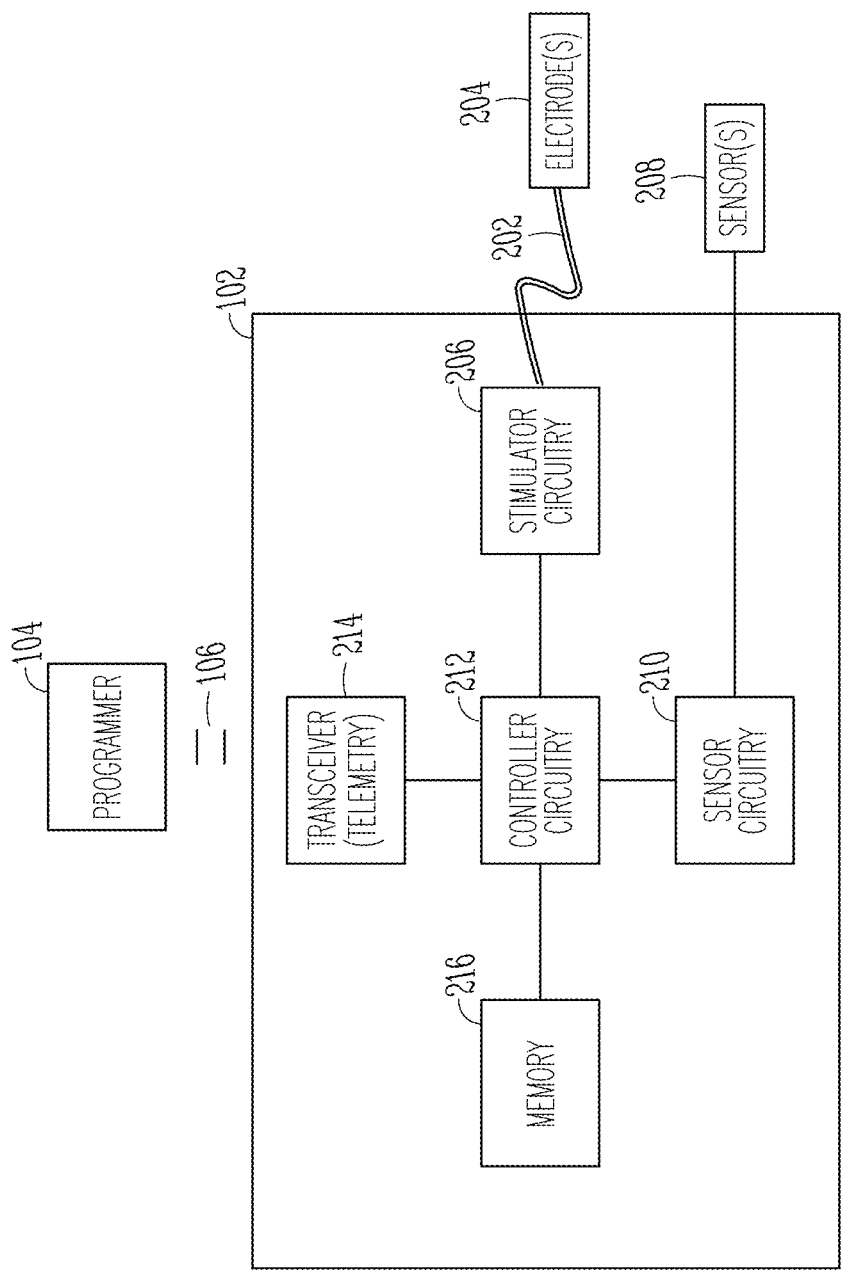
FIG. 2 illustrates an example of a system that includes an implantable medical device (IMD), such as the system of FIG. 1.

FIG. 2 illustrates an example of a system that includes an implantable medical device (IMD) and an external device such as the programmer 104 of FIG. 1. The IMD 102 may be coupled to at least a portion of a stimulation lead 202 having one or more electrodes 204 disposed on the lead 202. The leads 202 may include leads or electrodes that are in or on the heart, on vagus, hypoglossal, or phrenic nerves, on the carotid sinus, and may include subcutaneous electrodes (such as S-ICD or subcutaneous HF monitor), or other locations on or in the patient's body. In various embodiments, the lead 202 may include cuff electrode(s), helical electrode(s), or other electrode configuration configured to deliver monopolar, bipolar or multipolar stimulation. The lead 202 may have dimensions suitable to place the one or more electrodes 204 proximate to a site of a neural pathway. For example, the electrode(s) may be intravascular electrodes or may be configured to otherwise be placed proximate to a nerve. For example, electrode(s) may be placed in the internal jugular vein (IJV) to stimulate a cervical vagus nerve, or may be placed in the carotid sheath at a site proximate the vagus nerve of a patient. Monopolar delivery occurs when a selected electrode is activated along with a reference electrode amongst the electrodes 204, so that electrical energy is transmitted between the selected electrode and the reference electrode. Monopolar delivery may also occur when one or more of the selected electrodes are activated along with a large group of electrodes located from the electrode(s) 204 so as to create a monopolar effect; that is, electrical energy is conveyed from the selected electrode(s) 204 in a relatively isotropic manner. Bipolar delivery occurs when two of the electrodes 204 are activated as anode and cathode, so that electrical energy is transmitted between the activated electrodes. Multipolar delivery occurs when multiple electrodes 204 are activated.

The IMD 102 may include a stimulation circuitry 206, sensor circuitry 210, a controller circuitry 212, a transceiver/telemetry circuitry 214, and a memory 216. The stimulation circuitry 206 is electrically coupled to the electrodes 204 using conductors of the stimulation lead 202. The stimulation circuitry 206 delivers electrical signals to the electrodes 204 to stimulate the desired target to provide stimulation. The programmer 104 may be used to program stimulation parameters into the memory 216. The controller circuitry 212 may use the programmed stimulation parameter to control the stimulator circuitry 206 to generate the stimulation that corresponds to the programmed stimulation parameters.

The IMD 102 may include one or more sensor(s) 208 for sensing physiological parameters such as cardiac contractions which may be used to determine heart rate (beats per minute or bpm) or rhythm information, tissue impedance (ohms), intrinsic atrial-ventricular (AV) delay (seconds), heart sounds, respiratory sounds, pressure, respiration, acceleration (activity and posture), nerve traffic, chemical parameters, or the like. The sensor(s) 208 can be located external to the IMD 102 housing, or encapsulated within the IMD 102 housing. The sensor(s) 208 can be attached to the sensor circuitry 210. The sensor circuitry 210 can include various components, such as instrumentation amplifiers, signal filters, etc., that process the electrical signals for determining the physiological parameters.

The sensor circuitry 210 feeds the physiological parameters to the controller circuitry 212. The controller circuitry 212 controls various operations of the IMD 102 and can include programmable microprocessors, microcontrollers, or the like. For example, the controller circuitry 212 may be programmed to perform therapy and send control signals to the neural stimulator circuitry 206 for transmitting electrical stimulation pulses to the electrodes 204. The controller circuitry 212 analyzes the determined physiological parameters and other parameters inputted by the user using the programmer 104 to assess appropriate therapy regime and send control signals to neural stimulation circuitry 206 for transmitting stimulation pulses to the patient's target tissue.

The transceiver/telemetry circuitry 214 may communicate the determined physiological parameters to the programmer 104 located external to the patient's body. The telemetry circuitry 214 may use a suitable communication protocol, such as, the medical implant communication service (MICS) in the bandwidth of 402-405 MHz, for communicating with the programmer 104.

The memory 216 may be used to store the stimulation parameters received from programmer 104 and the physiological parameters determined by the sensor circuitry 210. For example, the memory 216 can store at least one year of daily lead impedance measurements and/or program usage. In another example, the memory can store lifetime energy use data for the device. In yet another example, the memory may store a list of measurements over time of a sensed parameter, for example, heart rate, for assessing the appropriate therapy regime.

The IMD 102 can be encased in a biocompatible metallic, polymeric, or composite housing (not shown), according to various embodiments. The housing protects the components of the IMD 102 from coming in contact with the patient's tissue. Additionally, the IMD 102 includes a power source such as a battery for delivering power to the IMD 102.

Figure 3:
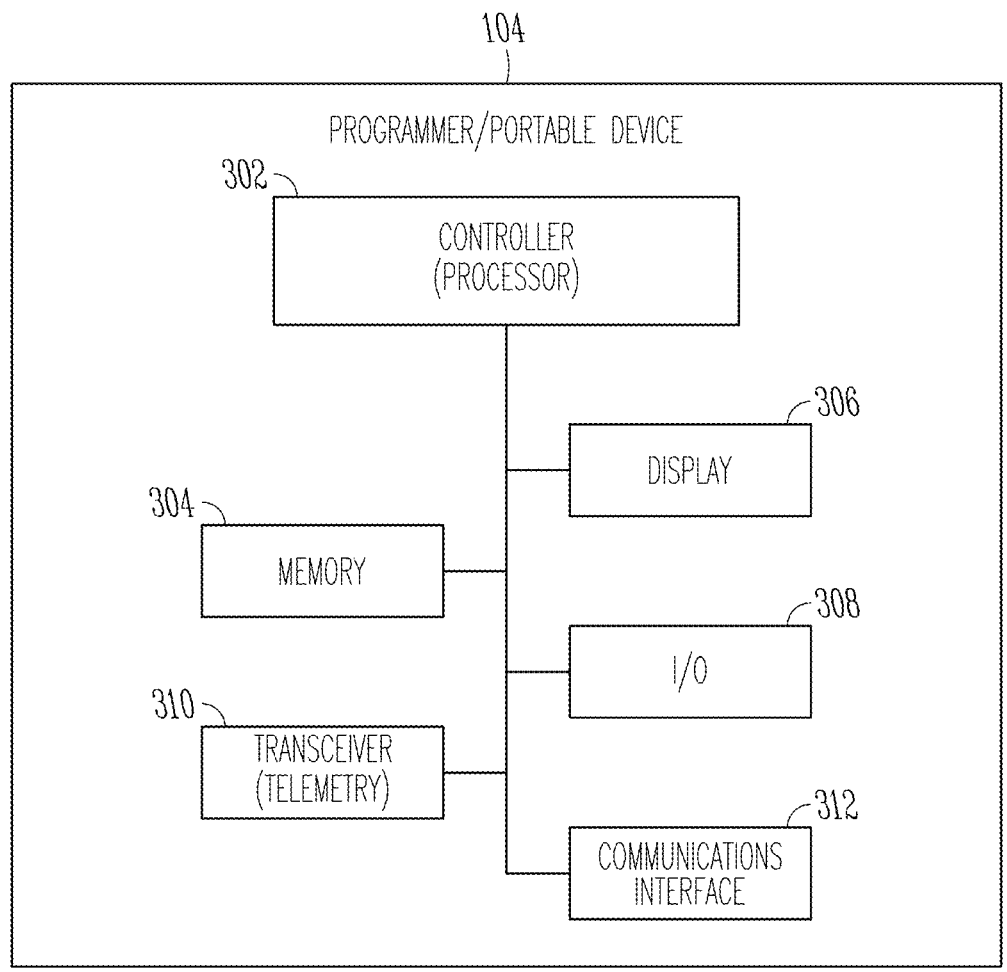
FIG. 3 illustrates an example of an external device, such as the programmer of FIG. 1.

FIG. 3 illustrates an example of an external device such as the programmer 104 of FIG. 1. The programmer 104 may be a portable device or hand held device that includes a controller/processor 302, a memory 304, a display 306, an input/output (I/O) unit 308, a transceiver/telemetry unit 310, and a communications interface 312. The programmer 104 may be housed within a polymeric, metallic or composite housing.

The controller 302 controls various operations of the programmer 104. The controller 302 may include any suitable computing device, for example, microprocessors, microcomputers, microcontrollers, digital signal processors, central processing units, state machines, logic circuitries, and/or any devices that manipulate signals based on operational instructions. Among other capabilities, the controller 302 may be configured to fetch and execute computer-readable instructions stored in the memory 304. Further, the controller 302 may be configured with standard or customized operating systems, such as, Microsoft Windows, Linux, UNIX, or the like, with one or more custom software installed to control the operations of other components of the programmer 104. The controller 302 may be a fixed or portable computing device such as a desktop computer or a laptop, tablet or phone. The telemetry unit 310 communicates with the IMD 102 using the telemetry link 106 (FIG. 1). In some embodiments, the telemetry unit 310 allows the programmer 104 to control and program the IMD 102. In addition, the telemetry unit 310 allows the programmer 104 to communicate with the IMD 102 (shown in FIG. 2).

VARIOUS EXAMPLES

An example (e.g. "Example 1") of a medical device for apnea discrimination may include a sensor configured to sense an impedance-based tidal volume signal to monitor a respiratory cycle of a patient, and a processor adapted to be connected to the sensor. The processor may be configured to detect a reduction in tidal swing using the sensed impendence to detect an apnea event and to compare a shape of the sensed signal to a stored signal shape to determine whether the detected apnea event is primarily an obstructive sleep apnea (OSA) event or primarily a central sleep apnea (CSA) event.

In Example 2, the subject matter of Example 1 may optionally be configured such that the stored signal shape includes a normal tidal swing shape for the patient.

In Example 3, the subject matter of Example 2 may optionally be configured such that, if the shape of the sensed signal is similar to the normal tidal swing shape, the apnea event is determined to be primarily a CSA event.

In Example 4, the subject matter of any one or any combination of Examples 2-3 may optionally be configured such that, if the shape of the sensed signal is not similar to the normal tidal swing shape, the apnea event is determined to be primarily an OSA event.

In Example 5, the subject matter of any one or any combination of Examples 1-4 may optionally be configured such that the stored signal shape includes a stored prior OSA waveform template.

In Example 6, the subject matter of any one or any combination of Examples 1-5 may optionally be configured such that the stored signal shape includes a sine wave or a square wave.

In Example 7, the subject matter of any one or any combination of Examples 1-6 may optionally be configured such that the processor is configured to use variability in low frequency components of a spectrum of at least one of R-R intervals, S1 amplitude, S2 amplitude, S3 amplitude or systolic time intervals to determine prevalence of primarily OSA events and primarily CSA events for the patient.

In Example 8, the subject matter of Example 7 may optionally be configured such that the processor is configured to use the variability to determine a likelihood of observing CSA or OSA on the next apnea event.

In Example 9, the subject matter of Example 8 may optionally be configured such that the processor is configured to adjust a discrimination threshold for the next apnea event based on the determined likelihood.

In Example 10, the subject matter of any one or any combination of Examples 1-6 may optionally be configured such that the processor is configured to track a set of spectral peaks on a spectrogram and use energies of tracked peaks to determine relative prevalence of primarily OSA events and primarily CSA events for the patient.

In Example 11, the subject matter of Example 10 may optionally be configured such that the processor is configured to use energy of the tracked peaks relative to total spectral energy to determine a likelihood of observing CSA or OSA on the next apnea event.

In Example 12, the subject matter of Example 11 may optionally be configured such that the processor is configured to adjust a discrimination threshold for the next apnea event based on the determined likelihood.

In Example 13, the subject matter of any one or any combination of Examples 1-12 may optionally be configured such that the device further includes a memory to store historical data of CSA events and OSA events for the patient.

In Example 14, the subject matter of Example 13 may optionally be configured such that the processor is configured to calculate a likelihood for each apnea event based on the historical data.

In Example 15, the subject matter of Example 14 may optionally be configured such that the processor is configured to use the calculated likelihood to determine whether the apnea event is primarily an obstructive sleep apnea (OSA) event or primarily a central sleep apnea (CSA) event.

An example (e.g. "Example 16") of a method for apnea discrimination may include sensing an impedance-based tidal volume signal to monitor a respiratory cycle of a patient, detecting a reduction in tidal swing using the sensed impendence to detect an apnea event, and, when the apnea event is detected, comparing a shape of the sensed signal to a stored signal shape to determine whether the apnea event is primarily an obstructive sleep apnea (OSA) event or primarily a central sleep apnea (CSA) event.

In Example 17, the subject matter of Example 16 may optionally be configured such that the stored signal shape includes a normal tidal swing shape for the patient.

In Example 18, the subject matter of Example 16 may optionally be configured such that the stored signal shape includes a stored prior OSA waveform template.

In Example 19, the subject matter of Example 16 may optionally be configured such that the stored signal shape includes a sine wave.

In Example 20, the subject matter of Example 16 may optionally be configured such that the stored signal shape includes a square wave.

In Example 21, the subject matter of Example 17 may optionally be configured such that, if the shape of the sensed signal is similar to the normal tidal swing shape, the apnea event is determined to be primarily a CSA event.

In Example 22, the subject matter of Example 17 may optionally be configured such that, if the shape of the sensed signal is not similar to the normal tidal swing shape, the apnea event is determined to be primarily an OSA event.

In Example 23, the subject matter of Example 16 may optionally be configured such that the method further includes calculating likelihood for each apnea event based on historical prevalence of CSA events and OSA events for the patient.

In Example 24, the subject matter of Example 23 may optionally be configured such that the method further includes using the calculated likelihood to determine whether the apnea event is primarily an obstructive sleep apnea (OSA) event or primarily a central sleep apnea (CSA) event.

In Example 25, the subject matter of Example 16 may optionally be configured such that the method further includes assigning a confidence score to the determination of whether the apnea event is primarily an obstructive sleep apnea (OSA) event or primarily a central sleep apnea (CSA) event.

An example (e.g. "Example 26") of a medical device for apnea discrimination may include a sensor configured to sense an impedance-based tidal volume signal to monitor a respiratory cycle of a patient, and a processor adapted to be connected to the sensor. The processor may be configured to detect a reduction in tidal swing using the sensed impendence to detect an apnea event and to compare a shape of the sensed signal to a stored signal shape to determine whether the detected apnea event is primarily an obstructive sleep apnea (OSA) event or primarily a central sleep apnea (CSA) event.

In Example 27, the subject matter of Example 26 may optionally be configured such that the processor is configured to use variability in low frequency components of a spectrum of at least one of R-R intervals, S1 amplitude, S2 amplitude, S3 amplitude or systolic time intervals to determine prevalence of primarily OSA events and primarily CSA events for the patient.

In Example 28, the subject matter of Example 27 may optionally be configured such that the processor is configured to use the variability to determine a likelihood of observing CSA or OSA on the next apnea event.

In Example 29, the subject matter of Example 28 may optionally be configured such that the processor is configured to adjust a discrimination threshold for the next apnea event based on the determined likelihood.

In Example 30, the subject matter of Example 26 may optionally be configured such that the processor is configured to track a set of spectral peaks on a spectrogram and use energies of tracked peaks to determine relative prevalence of primarily OSA events and primarily CSA events for the patient.

In Example 31, the subject matter of Example 30 may optionally be configured such that the processor is configured to use energy of the tracked peaks relative to total spectral energy to determine a likelihood of observing CSA or OSA on the next apnea event, and wherein the processor is configured to adjust a discrimination threshold for the next apnea event based on the determined likelihood.

An example (e.g. "Example 32") of a medical device for apnea discrimination may include a sensor configured to sense a parameter related to heart sounds of a patient, and a processor adapted to be connected to the sensor. The processor may be configured to use the sensed parameter to determine whether a detected apnea event is primarily an obstructive sleep apnea (OSA) event or primarily a central sleep apnea (CSA) event.

In Example 33, the subject matter of Example 32 may optionally be configured such that the parameter related to heart sounds of the patient includes variability in low frequency components of a spectrum of at least one of R-R intervals, S1 amplitude, S2 amplitude, S3 amplitude or systolic time intervals.

In Example 34, the subject matter of Example 32 may optionally be configured such that the device further includes a memory to store historical data of CSA events and OSA events for the patient.

In Example 35, the subject matter of Example 34 may optionally be configured such that the processor is configured to calculate likelihood for each apnea event based on the historical data and to use the calculated likelihood to determine whether the apnea event is primarily an obstructive sleep apnea (OSA) event or primarily a central sleep apnea (CSA) event.

One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method.

This application is intended to cover adaptations or variations of the present subject matter. It is to be understood that the above description is intended to be illustrative, and not restrictive. For example, the present subject matter can be applied to other medical procedures where heating or ablation of tissue is desired. The scope of the present subject matter should be determined with reference to the appended claims, along with the full scope of legal equivalents to which such claims are entitled.

What is claimed is:

1. A system, comprising:
    a sensor configured to sense an impedance-based tidal volume signal to monitor a respiratory cycle of a patient; and
    an external system including a device configured to communicate with the sensor, the external system including a processor configured to detect a reduction in tidal swing using the sensed impendence to detect an apnea event and comparing a shape of the reduction in tidal swing to a stored signal shape to determine whether the detected apnea event is primarily an obstructive sleep apnea (OSA) event or primarily a central sleep apnea (CSA) event.

2. The system of claim 1, wherein the external system is configured to compare a stored signal shape to the signal to determine whether the detected apnea event is primarily an OSA event or primarily a CSA event.

3. The system of claim 2, wherein the stored signal shape includes a normal tidal swing for the patient.

4. The system of claim 2, wherein the stored signal shape includes a stored prior OSA waveform template.

5. The system of claim 2, wherein the stored signal shape includes an ideal sine wave as a surrogate for a CSA waveform template.

6. The system of claim 1, wherein the device includes a diagnostic device.

7. The system of claim 1, wherein the device includes a stimulator.

8. The system of claim 1, wherein the device includes a wearable device.

9. The system of claim 8, wherein the wearable device includes a patch.

10. The system of claim 8, wherein the wearable device includes a vest.

11. A method for apnea discrimination, the method comprising:
    sensing an impedance-based tidal volume signal using a sensor to monitor a respiratory cycle of a patient; and
    using an external system to communicate with the sensor and to process the sensed parameter to detect a reduction in tidal swing using the sensed impendence to detect an apnea event and comparing a shape of the reduction in tidal swing to a stored signal shape to determine whether the detected apnea event is primarily an obstructive sleep apnea (OSA) event or primarily a central sleep apnea (CSA) event.

12. The method of claim 11, comprising using a processor in an implantable stimulator in communication with the sensor to process the sensed parameter.

13. The method of claim 11, comprising using a processor in a nerve stimulator in communication with the sensor to process the sensed parameter.

14. The method of claim 11, comprising using a processor in an implantable diagnostic device in communication with the sensor to process the sensed parameter.

15. The method of claim 11, comprising using a processor in a wearable device in communication with the sensor to process the sensed parameter.

16. The method of claim 11, comprising using a processor in an external medical device in communication with the sensor to process the sensed parameter.

17. The method of claim 11, further comprising using the processor to determine a mix or ratio of OSA and CSA for the patient.

18. The method of claim 17, further comprising using a display connected to the processor to present the mix or ratio of OSA and CSA to a clinician for diagnostic assistance.

19. The method of claim 11, further comprising using a memory connected to the processor to store historical data of CSA events and OSA events for the patient.

20. The method of claim 19, further comprising using the processor to calculate likelihood for each apnea event based on the historical data and to use the calculated likelihood to determine whether the apnea event is primarily an OSA event or primarily a central sleep apnea CSA event.

* * * * *